US005705701A

United States Patent [19]

Sunagawa

[11] Patent Number: 5,705,701
[45] Date of Patent: Jan. 6, 1998

[54] PROCESS FOR PRODUCING TRIMETHYLSULFOXONIUM BROMIDE

[75] Inventor: Kazuhiko Sunagawa, Iwaki, Japan

[73] Assignee: Kureha Kagaku Kogyo Kabushiki Kaisha, Japan

[21] Appl. No.: 773,063

[22] Filed: Dec. 24, 1996

[30] Foreign Application Priority Data

Dec. 28, 1995 [JP] Japan ................... 7-353265

[51] Int. Cl.$^6$ ................................ C07C 315/04
[52] U.S. Cl. ................................ 568/27
[58] Field of Search ........................ 568/27

[56] References Cited

U.S. PATENT DOCUMENTS 4,141,920 2/1979 Dryden ........................... 568/74
4,625,065 11/1986 Heather.

OTHER PUBLICATIONS

CA69:18780, 1968 Abst of "2 Analog & halomethylketones from acyloxsulfonium", author M. Cory.
CA94: 7183 1978 "Abst of Detrom & control of explosion of hazards involved in prep of formethylsufoxonium bromide" author Scaro.
CA 80:73882 1973 Abst of "Chem hazards in preparation of trimethylsulfoxonium bromide" Scaro.
CA 80:69812 (1973) "Abst–Laboratory Explosion".

*Primary Examiner*—C. Warren Ivy
*Assistant Examiner*—Jean F. Vollano
*Attorney, Agent, or Firm*—Nixon & Vanderhye

[57] ABSTRACT

In a process for producing trimethylsulfoxonium bromide by reacting dimethyl sulfoxide and methyl bromide, methyl bromide is added to a mixture of dimethyl sulfoxide and a stabilizing agent under atmospheric pressure intermittently or continuously so that the final molar ratio of methyl bromide to dimethyl sulfoxide becomes 0.40:1 to 0.70:1, with the temperature of dimethyl sulfoxide being maintained at a temperature of 50° to 75° C. This process can realize a reduction of reaction time, an improvement of yield and establishment of safety of producing operations.

9 Claims, No Drawings

PROCESS FOR PRODUCING TRIMETHYLSULFOXONIUM BROMIDE

BACKGROUND OF THE INVENTION

The present invention relates to a process for producing trimethylsulfoxonium bromide which is useful as an intermediate of fungicidal azole derivatives.

The trimethylsulfoxonium bromide is a compound which is obtained by reacting dimethyl sulfoxide with methyl bromide and is useful as an intermediate of fungicidal azole derivatives (Japanese Patent Application Laid-open (Kokai) No. 1-301664 corresponding to European Patent No. 329397).

The reaction for synthesizing an oniumbromide such as trimethylsulfoxoniumbromide from methyl bromide and a hetero-atom compound is usually carried out in a sealed tube by initially feeding the starting compounds into the tube.

For instance, Tetrahedron Letters, No. 20, 2501–2502 (1968) describes that trimethylsulfoxoniumbromide is synthesized by heating dimethyl sulfoxide and methyl bromide in a sealed tube at 80° to 90° C. for 48 hours.

Further, use of the reaction-improving agents (stabilizing agents) such as trimethyl orthoformate, etc. in the reaction of dimethyl sulfoxide and methyl bromide has been proposed in Catalysis in Organic Syntheses, Vol. 7, 301–309 (1980), and U.S. Pat. No. 4,141,920.

Generally, use of a sealed tube or a pressure vessel is recommended for carrying out reaction for synthesizing trimethylsulfoxoniumbromide in a high yield despite variation in reaction temperature and/or reaction time. However, U.S. Pat. No. 4,141,920 reports that in the reaction of dimethyl sulfoxide and methyl bromide, when the mixture is heated to approximately 66° C., there takes place a violent reaction, causing vehement formation of by-products such as hydrogen bromide. As a result, this vehement formation of by-products may trigger the chain decomposition of dimethyl sulfoxide and could even cause explosion of the reaction vessel. Further, the following facts are also known.

(a) When dimethyl sulfoxide (water content=100 PPM) is reacted with methyl bromide in a molar ratio of 1:0.5 at 60° C. in a pressure reaction vessel (closed vessel, pressure bottle, etc.), the internal pressure of the vessel, which is about 3 atom at the start of the reaction, decreases to about 1.3 atom after 90 hours from the start of the reaction. If heating is further continued, there takes place the chain decomposition of dimethyl sulfoxide after 212 hours from the start of the reaction to cause breakage of the reaction vessel.

(b) This chain decomposition is influenced by water in dimethyl sulfoxide, so that when dimethyl sulfoxide with a water content of 900 ppm is used, the vessel suffers breakage due to the chain decomposition after 98 hours from the start of the reaction.

(c) The reaction-improving agents (stabilizing agents) such as trimethyl orthoformate suppress the chain decomposition by capturing the by-product hydrogen bromide and water.

(d) By reacting a mixture containing 0.025 mol of trimethyl orthoformate and 0.5 mol of methyl bromide per one mol of dimethyl sulfoxide in a pressure reaction vessel at 60° C. for 50 hours, trimethylsulfoxoniumbromide can be obtained in an isolation yield of 80%.

(e) By reacting a mixture containing 0.019 mol of trimethyl orthoformate and 0.39 mol of methyl bromide per one mol of dimethyl sulfoxide under atmospheric pressure at room temperature for 5 weeks, trimethylsulfoxonium bromide can be obtained in an isolation yield of 50%.

With the conventional technology mentioned above, however, it is essential to use a pressure vessel for the reaction in order to obtain trimethylsulfoxoniumbromide at a high yield. Accordingly, a process capable of producing trimethylsulfoxoniumbromide in a high yield by conducting the reaction under atmospheric pressure has been desired. Reduction of the reaction time has also been required.

As a result of extensive researches of the present inventors, it has been found that in the process for producing trimethylsulfoxonium bromide, by reacting dimethyl sulfoxide with methyl bromide by adding methyl bromide to a mixture of dimethyl sulfoxide and a stabilizing agent under atmospheric pressure intermittently or continuously so that the final molar ratio of methyl bromide to dimethyl sulfoxide becomes 0.40:1 to 0.70:1, with the temperature of dimethyl sulfoxide being maintained at a temperature of 50° to 75° C., the reduction of reaction time, the improvement of yield and the establishment of safety in producing operations can be realized. The present invention has been attained on the basis of this finding.

SUMMARY OF THE INVENTION

It is an object of the present invention to provide a process for producing trimethylsulfoxoniumbromide in which the reaction can be carried out under atmospheric pressure and which is capable of reducing the reaction time, elevating the yield and enhancing the safety of the producing operations.

In order to attain the aim, in an aspect of the present invention, there is provided a process for producing trimethylsulfoxoniumbromide, which comprises reacting dimethyl sulfoxide with methyl bromide by adding methyl bromide to a mixture of dimethyl sulfoxide and a stabilizing agent intermittently or continuously under atmospheric pressure so that the final molar ratio of methyl bromide to dimethyl sulfoxide becomes 0.40:1 to 0.70:1, with the temperature of dimethyl sulfoxide being maintained at a temperature of 50° to 75° C.

DETAILED DESCRIPTION OF THE INVENTION

A detailed description of the present invention follows.

The water contents of the starting compounds used in the present invention, viz. dimethyl sulfoxide, methyl bromide and a stabilizing agent are all not more than 400 ppm, preferably not more than 200 ppm, more preferably not more than 100 ppm.

The drying method of the starting compounds used in the present invention is not limited but, for instance, the following methods are exemplified.

(i) A method of using molecular sieves as desiccant.

(ii) A method comprising adding a stabilizing agent to dimethyl sulfoxide and heating the mixture to distill away the low-boiling point compounds.

In the present invention, methyl bromide is used in an amount of 0.40 to 0.70 mol, preferably 0.45 to 0.55 mol, more preferably 0.48 to 0.53 mol based on one mol of dimethyl sulfoxide. In case the amount of methyl bromide used is less than 0.40 mol based on one mol of dimethyl sulfoxide, the amount of the reaction product dissolved in the filtrate is increased correspondingly, when the product is isolated by filtration, resulting in a reduced isolation yield. On the other hand, in case methyl bromide is used in excess of 0.70 mol, a long time is required to complete the reaction. In either case, the object of the present invention can not be accomplished.

The stabilizing agent used in the present invention is not limited, but trimethyl orthoformate, triethyl orthoformate, tripropyl orthoformate, tetramethyl orthocarbonate, tetraethyl orthocarbonate, tetraisopropyl orthocarbonate and tetrapropyl orthocarbonate may be exemplified. The stabilizing agent is used singly or as a mixture of two or more. The stabilizing agent enhances the specific effects such as reduction of reaction time, elevation of yield and establishment of safety of producing operations. Of the stabilizing agents mentioned above, trimethyl orthoformate is more preferred. This compound is used in an amount of 0.002 to 0.05 mol, preferably 0.004 to 0.02 mol based on one mol of dimethyl sulfoxide.

Reaction vessel is also not specified in the present invention. For instance, a glass lining vessel can be used for the reaction of the present invention. A condenser is equipped to the reaction vessel. This condenser is preferably of the structure in which a T-tube is equipped to the top end of the condenser, with both ends of the said T-tube being connected to the rubber or silicone tubes from one of which is introduced an inert gas such as nitrogen or argon gas while a glass tube is secured to the end of the other rubber or silicone tube, with the free end of the said glass tube being immersed in silicone oil to prevent inflow of the atmospheric air.

It is preferred that a small amount of an inert gas is bubbled continuously in the mixture of the starting compounds to make an inert gas atmosphere in the reaction vessel and the reaction is carried out in such an atmosphere.

A prescribed amount of dimethyl sulfoxide and optionally a prescribed amount of a stabilizing agent are supplied into the reaction vessel and heated to 50° to 70° C. with stirring. Into dimethyl sulfoxide or the above mixture is added a predetermined amount of gaseous or liquid methyl bromide intermittently or continuously so that the temperature of dimethyl sulfoxide or the said mixture will be maintained at 50° to 70° C., and that gentle reflux may be kept in the condenser (which is usually cooled bypassing a coolant of a temperature of −10° to −50° C.).

Since the reaction mixture assumes slurry-like during addition of methyl bromide, the mixture is preferably stirred so as to sufficiently mix up the slurry during the reaction.

After a prescribed amount of methyl bromide has been added, the resultant mixture is further stirred at a temperature of 50° to 70° C. for 3 to 18 hours.

Then, the reaction mixture is cooled to room temperature, the insoluble matters are filtered out and washed with an organic solvent such as benzene, toluene, xylene or the like, and the washings are removed by filtration to obtain a residual white substance. The obtained substance is dried in vacuo at 30° to 60° C. In this way, there can be obtained the objective product with a purity of about 99% in an isolation yield of not less than 90%.

As for the reaction time in the present invention, a period of not less than 50 hours, usually 100 to 160 hours is required for both operations of adding methyl bromide and ensuing stirring. Although the reaction time in the present invention is longer than the period (approximately 50 hours) required for the conventional reactions under low-degree high-pressure (about 3 kg/cm²G), the reaction according to the present invention can be completed in a far shorter time than required for the conventional reactions (e.g. about 5 weeks) conducted under atmospheric pressure at room temperature.

The reaction according to the present invention can be carried out under atmospheric pressure and is industrially advantageous in terms of product purity, isolation yield and safety of producing operations.

The benefits of the present invention that allows practice of the reaction under atmospheric pressure include the followings besides abatement of restrictions for pressure resistance ability of the reaction vessel.

Since the boiling point of methyl bromide is 4.6° C. and that of hydrogen bromide is −66.8° C., it is possible to remove the by-products from the reaction mixture by adjusting the temperature of the coolant in the condenser. Particularly, since hydrogen bromide is a compound which has an incentive to the chain decomposition of dimethyl sulfoxide, quick removal thereof from the reaction mixture is desirable not only from the viewpoint of enhancement of isolation yield but also from the viewpoints of product purity and operational safety of the production process.

According to the process of production of trimethylsulfoxoniumbromide of the present invention, it is possible to obtain high-purity trimethylsulfoxoniumbromide in a high isolation yield by a reaction under atmospheric pressure with a short reaction time and by safe operations.

EXAMPLES

The present invention is further illustrated with reference to the examples, but it will be recognized that these examples are given for the purpose of illustration only, and are not to be construed as limiting the scope of this invention in any way.

Example 1

Production of trimethylsulfoxonium bromide 47 kg of dimethyl sulfoxide (water content: 100 ppm) and 500 ml of trimethyl orthoformate (water content: not more than 100 ppm) were supplied into a 100-liter glass lining reaction vessel adapted with a condenser (cooled bypassing a −30° C. coolant (TSF 451-5A, produced by Toshiba Silicone Co., Ltd.), with the upper portion communicated with the reaction vessel being filled with a nitrogen stream) and the resultant mixture was heated to 60° to 65° C.

Then, 30 kg of methyl bromide (water content: not more than 100 ppm) were added to the heated mixture from a bomb through a tube inserted into the said mixture, the addition being made at such a rate that the mixture would be refluxed gently in the condenser while maintaining the mixture temperature at 60° to 65° C. The period for completing the addition of methyl bromide was 130 hours. As the reaction mixture assumed slurry-like during addition, the reaction mixture was stirred to sufficiently mix up the slurry. After the whole amount of methyl bromide has been added, the resultant reaction mixture was further stirred at the same temperature for 10 hours.

The resulting yellow reaction mixture was cooled to room temperature and the insoluble matters were filtered out. The precipitate was washed with 74.4 liters of toluene, then the washings were removed by filtration under reduced pressure, and after additional washing, the obtained precipitate was dried in vacuo at 50° C. to obtain 49.6 kg of the objective product (purity: over 99% (measured by ion pair chromatography); yield: 90.5%).

Referential Production Example 1

Synthesis of 5-(4-chlorobenzyl)-2,2-dimethyl-1-(1 H-1,2,4-triazol-1-ylmethyl)cyclopentanol Using trimethylsulfoxonium bromide obtained in Example 1, the captioned compound was synthesized according to the method described in Japanese Patent Application Laid-open (Kokai) No. 1-301664 (corresponding to European Patent No. 329397).

200 ml of N-methyl-2-pyrrolidinone and 72 g of 60% oily sodium hydride were supplied into a 2-liter four-necked flask while passing nitrogen therethrough, and stirring the resultant mixture and maintaining the temperature of the mixture not more than 80° C., a mixed solution of 103.6 g of 1,2,4-triazole and 250 ml of N-methyl-2-pyrrolidinone was added dropwise.

After the dropwise addition has been completed, the obtained mixture was further stirred for 30 minutes and then, maintaining the temperature of the mixture not more than 80° C., 44.5 g of t-butanol was added dropwise. After the dropwise addition of t-butanol has been completed, the obtained mixture was stirred successively for 30 minutes and heated to 115° C., followed by further addition thereto of 246.3 g 5-(4-chlorobenzyl)-2,2-dimethyl-1-cyclopentanone having a purity of 96.1%. Then, 208 g of trimethylsulfoxonium bromide and 28.8 g of sodium t-butoxide were added by piecemeal over a period of 5 hours, and thereafter the resultant mixture was reacted for 3 hours.

The reaction mixture was cooled, mixed well with 700 ml of water and extracted twice with 700 ml of toluene.

The toluene layer was washed thrice with 1,400 ml of water to obtain 1,441 g of a toluene solution containing 175 g of cis-form of the captioned compound and 44 g of transform thereof.

Separation of cis-form of 5-(4-chlorobenzyl)-2,2-dimethyl-1-(1 H-1,2,4-triazol-1-ylmethyl) cyclopentanol To 100 g of the toluene extract containing the cis-form and the trans-form of 5-(4-chlorobenzyl)-2,2-dimethyl-1-(1 H-1,2,4-triazol-1-ylmethyl)cyclopentanol obtained in the described above, was added 1.39 g of 95% sulfuric acid (the molar ratio of sulfuric acid to the sum of the cis-form and the trans-form in 100 g of the toluene extract=0.3), and the obtained mixture was subjected to azeotropic dehydration by heating under reflux. 5 hours later, the ratio of the cis-form to the trans-form became 98:2, whereat the resultant mixture was cooled and mixed well with 50 g of 3% sodium hydroxide solution.

The toluene layer was washed thrice with water and dried over anhydrous sodium sulfate, and then toluene was distilled away under reduced pressure to obtain 23.27 g of residue.

By HPLC analysis, it is recognized that the obtained residue contained 51.4 wt % of cis-form and 1.1 wt % of transform. From these values, the cis-form yield from the toluene extract was determined to be 98.5% and the transform decomposition percentage was 91.8%.

To the obtained residue, 80 ml of methylcyclohexane was added and dissolved at 75° C., and the resultant mixture was cooled to 0° C. at a cooling rate of 10° C./60 min. The precipitated crystals were filtered out, washed with 35 ml of methylcyclohexane and dried at 65° C. to obtain 11.64 g of crystals (cis-form purity=97%; overall cis-form yield from toluene extract=93.0%; trans-form content=0.9%).

What is claimed is:

1. A process for producing trimethylsulfoxonium bromide which comprises reacting dimethyl sulfoxide with methyl bromide by adding methyl bromide to a mixture of dimethyl sulfoxide and a stabilizing agent under atmospheric pressure intermittently or continuously so that the final molar ratio of methyl bromide to dimethyl sulfoxide will become 0.40:1 to 0.70:1, with the temperature of dimethyl sulfoxide being maintained at a temperature of 50° to 75° C., to react dimethyl sulfoxide and methyl bromide.

2. The process according to claim 1, wherein after the addition of methyl bromide has been completed, the reaction mixture is stirred at a temperature of 50° to 75° C. for 3 to 18 hours.

3. The process according to claim 1, wherein the water contents of dimethyl sulfoxide and methyl bromide as starting materials are both not more than 400 ppm.

4. The process according to claim 1, wherein the amount of methyl bromide used is 0.45 to 0.55 mol based on one mol of dimethyl sulfoxide.

5. The process according to claim 4, wherein the amount of the stabilizing agent used is 0.002 to 0.05 mol based on one mol of dimethyl sulfoxide.

6. The process according to claim 1, wherein at least one stabilizing agent selected from the group consisting of trimethyl orthoformate, triethyl orthoformate, tripropyl orthoformate, tetramethyl orthocarbonate, tetraethyl orthocarbonate, tetraisopropyl orthocarbonate and tetrapropyl orthocarbonate is added to dimethyl sulfoxide in an amount of 0.002 to 0.05 mol based on one mol of dimethyl sulfoxide, and then methyl bromide is added to the resultant mixture in such a manner that gentle reflux is maintained in the condenser.

7. The process according to claim 6, wherein the stabilizing agent is trimethyl orthoformate.

8. The process according to claim 6, wherein the amount of the stabilizing agent used is 0.004 to 0.02 mol based on one mol of dimethyl sulfoxide.

9. The process according to claim 6, wherein reflux is carried out using a condenser cooled by passing a coolant of a temperature of −50° to −10° C.

* * * * *